(12) United States Patent
Hein

(10) Patent No.: US 6,517,578 B2
(45) Date of Patent: Feb. 11, 2003

(54) GRAFT SUSPENSION DEVICE

(75) Inventor: Dietmar Hein, Kiel (DE)

(73) Assignee: Atlantech Medical Devices Limited, Harrogate (GB)

( * ) Notice: Subject to any disclaimer, the term of this patent is extended or adjusted under 35 U.S.C. 154(b) by 0 days.

(21) Appl. No.: 09/732,783

(22) Filed: Dec. 11, 2000

(65) Prior Publication Data

US 2001/0041938 A1 Nov. 15, 2001

(30) Foreign Application Priority Data

Dec. 15, 1999 (GB) ............................................. 9929599

(51) Int. Cl.$^7$ .................................................. A61F 2/08
(52) U.S. Cl. .............................. 623/13.13; 623/13.14; 623/13.2; 606/232
(58) Field of Search ............................ 623/13.13, 13.12, 623/13.14, 13.15, 13.19, 13.2, 13.11; 606/72, 151, 232

(56) References Cited

U.S. PATENT DOCUMENTS

| | | | | |
|---|---|---|---|---|
| 3,973,277 A | * | 8/1976 | Semple et al. | 623/13.14 |
| 4,149,277 A | * | 4/1979 | Bokros | 623/13.2 |
| 4,187,558 A | * | 2/1980 | Dahlen et al. | 623/13.14 |
| 5,139,520 A | * | 8/1992 | Rosenberg | 606/102 |
| 5,152,790 A | * | 10/1992 | Rosenberg et al. | 623/13 |
| 5,609,634 A | * | 3/1997 | Voydeville | 606/61 |
| 5,645,588 A | | 7/1997 | Graf et al. | |
| 5,769,894 A | | 6/1998 | Ferragamo | |
| 6,110,207 A | * | 8/2000 | Eichhorn et al. | 623/13.14 |

FOREIGN PATENT DOCUMENTS

| | | |
|---|---|---|
| EP | 0 865 774 A1 | 9/1998 |
| WO | 98/12991 | 2/1998 |
| WO | 98/12992 | 4/1998 |

* cited by examiner

Primary Examiner—Paul B. Prebilic
(74) Attorney, Agent, or Firm—Nixon & Vanderhye

(57) ABSTRACT

The invention describes a graft suspension device 2 for suspending a ligament in a bone hole. The suspension device 2 comprises a first loop 4 and second loop 6 suspended from an anchor 8 and has a cradle 10 at the opposite end of the loop to the anchor. Ligament grafts (not shown) are looped over the cradle 10 and loose ends 30,32 may be pulled by finger loops 22, 24 whereby the surgeon can adjust the distance of the cradle 10 from the anchor 8 thereby tensioning the grafts as desired.

15 Claims, 2 Drawing Sheets

GRAFT SUSPENSION DEVICE

The present invention relates to a graft suspension device, in particular, but not exclusively, to a graft suspension device for graft fixation such as tendon or ligament fixation.

BACKGROUND OF THE INVENTION

Due to increasing involvement of people with active sport, injuries are becoming increasingly common where tissues such as ligaments or tendons tear or detach from bone. Surgical techniques have been developed to reconstruct such soft tissues arid to re-attach them to the relevant bone. One of the most common types of such injuries is tearing of the anterior cruciate ligament (ACL). The ACL connects the femur to the tibia at the centre of the knee joint. Reconstruction of such tissues generally involves replacement with a graft such as autologous or artificial tendon. An autologous tendon graft may be taken from the patients patella tendon or, alternatively, the Semi-tendinosus or Semitendinosus/Gracilis may be utilised. One method of graft fixation within the femoral tunnel involves the use of a button fixation device on the anterolateral femoral cortex which is attached to the graft by means of sutures or tapes through a tunnel in the femur. U.S. Pat. No. 5,645,588 describes a technique whereby the ligament anchor may be threaded through a femoral tunnel formed through the femur from the centre of the knee but such still involves the use of sutures attached directly to the fixation device on the outside of the femur above the knee and through which the graft is looped before the passing out of the femoral tunnel before being secured to the tibia. A particularly important issue in the grafting operation is that the graft is fixed in the bone tunnel at the required tension. Inappropriate tensioning of the graft will affect the success of the operation. In practice, tensioning devices may be utilised but, having achieved the required tension, it is then necessary for the surgeon to tie off the suture and the tying of knots introduces errors into the process and also may result in some subsequent stretch in the suture causing an inappropriate tension in the graft. Furthermore, tying of knots during the procedure also increases surgical time and is inconvenient.

SUMMARY OF THE INVENTION

According to a first aspect of the present invention, there is provided a graft suspension device for a ligament fixation graft comprising suspension means for suspending a ligament in a bone hole, the suspension means having anchoring means at one end thereof, ligament cradling means at the other end thereof and an adjustable length suspension line therebetween, the suspension line being formed into at least two loops engaging the said anchoring means, wherein the cradling means comprises a sleeve portion through which the ends of at least a first of the said at least two loops are threaded in opposite directions to cross-over in the sleeve portion and emerge at opposite ends of the said sleeve portion.

Preferably, the sleeve portion forms part of a second of the said at least two loops. Preferably, the sleeve portion forms an integral part of the said second loop. The sleeve portion may be part of a second hollow loop whereby inlet and outlet eyes are formed in the hollow loop at spaced intervals to thereby form a sleeve portion through which the ends of the said first loop may be threaded ie. one end of the loop may be threaded through the sleeve from the first eye to the second eye and the other end may be threaded through the sleeve from the second eye to the first eye. As the second loop is hollow, a braided loop is preferred. An aperture need not be formed in the said second loop if the ends of the first loop may be threaded therethrough by passing through gaps between adjacent threads of the braid.

For the avoidance of doubt, references to first and second loop are intended to distinguish the loops from each other and are not an indication of the order in which the loops are engaged with the anchor. In fact, preferably, the second loop is formed and engaged with the anchor before the said first loop.

Preferably, the ends of the suspension line remain separate from each other but it is envisaged that they could be connected after adjustment of the suspension line or possibly before, if preferred.

Preferably, the ends of the line are adapted to include gripping elements to allow each end to be held and adjusted with respect to the sleeve portion to thereby effect shortening of the overall loop length and tensioning of the ligament.

Preferably, the loops of the suspension line are formed from a single line so that a loop is formed and then threaded back through the anchor to form a further loop which is completed by threading through the sleeve so that the ends of the further loop cross over therein.

Preferably, the suspension line is a suture, preferably, a hollow suture comprising a plurality of threads, preferably, the threads are plaited together to form a hollow tubular suture such as a braided suture.

Preferably, the sleeve portion is sufficiently long to suspendingly accommodate a ligament fixation graft thereover but, preferably, sufficiently short to facilitate efficient adjustment of the suspension line length by urging the ends of the said first loop away from the said sleeve portion.

Generally, adjustment of the loop will take place prior to locating and anchoring of the suspension device and graft in the bone hole. However, it is also envisaged that it may be desired to adjust the suture length and graft tension in the bone hole.

In this regard, it should be noted that if the sleeve portion is too long the ends of the sleeve may be urged against the closed end of the bone tunnel which may hinder anchoring and adjustment thereof.

It is envisaged that the ends may be urged away from the sleeve from a position of the ends both above the opposite side of the bone to the bone tunnel opening or below the entrance to the bone hole. One possibility is for the ends to emerge up through the suture passing channel or to be simply not passed through the channel so that they remain at the entrance to the bone hole.

As both ends of the line are threaded through the sleeve portion, the sleeve portion effectively incorporates at least three thicknesses of line ie the two end portions threaded through it and the sleeve portion itself. Advantageously, this provides a thicker piece of line which forms a cradle for a suspension graft located thereover and prevents the line cutting into the graft.

Preferably, the anchoring means is secured to the outside of the opposite side of the bone to the opening to the bone tunnel, wherein, preferably, the cradling means is located. It is envisaged that in addition to pre-locating and pre-anchoring adjustment, the cradling means is located in the bone tunnel for adjustment of the loop and tensioning of the graft located therein and over the said cradle.

According to a second aspect of the present invention, there is provided a method of producing a device according to the first aspect of the present invention comprising the steps of:

forming a hollow suspension line into a loop having overlapping ends;

forming a pair of spaced apertures in the said suspension line loop to form a sleeve portion therein opposite the overlapping ends and forming the overlapping ends into a further loop comprising threading each of the ends through the said sleeve portion in opposite directions to cross over in the sleeve portion and emerge at opposite ends of the said sleeve portion.

Preferably, the method includes the further step of adapting the ends, preferably, after forming the second loop, to include gripping elements to simplify adjustment of the position thereof with respect to the sleeve portion. Preferably, the loop length is adjusted by pulling the respective ends apart from each other to thereby shorten the loop. Preferably, the ends may be formed into gripping members by forming a further loop at the said end, preferably, a finger loop is formed.

Preferably, the suspension line is a suture for use in ligament fixation.

The anchoring means may be of conventional construction for securement to the outside of a bone and, preferably includes a pair of apertures through which the ends of the suspension suture may be threaded during loop formation. The cradle may be formed by the space between the pair of apertures in the hollow suture. Preferably, the cradle is located substantially midway along the length of the suture. The initial loop may be formed by locating the cradle part of the suture opposite the anchoring means and threading the first end of the suture through a first aperture of a pair of spaced apertures on the anchoring means and threading the second end of the suture through the second aperture of the pair of spaced apertures. A further loop may be formed by first threading each of the ends of the suture back through the anchoring means, respectively through the alternative aperture of the pair of apertures, and secondly, threading each end through apertures formed in the initial loop and through the sleeve portion therebetween, each end being so threaded in opposite directions to cross over in the sleeve portion and emerge at the opposite end thereof. The first and second loop between the anchoring means and the cradle are thereby formed.

Advantageously, the ends may be of sufficient length to pass out through the entrance to a bone tunnel at the closed end of which the cradle is located to allow the operator to tension the graft or simply adjust the loop length by pulling on the said ends. This allows ease of tensioning and loop length adjustment typically, pre-operatively and/or, possibly, intra-operatively. Possibly due to the loop being under tension in use, after tensioning of the graft and release of the ends, the loop surprisingly does not significantly re-extend again and this provides the further advantage that the ends do not require simultaneous tensioning and tying off but may be tied off subsequently without significantly affecting tension.

According to a third aspect of the present invention, there is provided a method of graft fixation comprising the steps of:

forming a bone hole suitable for graft fixation therein;

locating a graft over the cradle end of a graft suspension device in accordance with the first aspect of the present invention, and anchoring the said device to the bone so that the cradle end thereof extends into such a bone hole from the closed end thereof with the graft suspended therefrom in the direction of the entrance to the bone hole.

Adjusting the ends of the suspension device to obtain the suspension loop length required is typically carried out prior to location of the graft in the bone hole and anchoring thereof, however, it may, alternatively, or additionally, take place after anchoring of the said device.

Preferably, the loop length is adjusted to be in excess of that required for graft fixation prior to use so that the loop ends may be simply pulled to shorten the loop to the required length either before or during fixation.

Preferably, the suspension device is located in the bone tunnel via a suture passing channel and, preferably, anchored using button fixation.

Preferably, the suspension device loops are formed from a braided suture. Advantageously, braided sutures are hollow and tubular which provides the necessary features for a cradle sleeve portion.

The invention also extends, in a fourth aspect, to an adjustable loop for use in tensioning during surgery comprising suspension means for engagement with a member to be tensioned, the suspension means having anchoring means at one end thereof, a member to be tensioned engagement portion at the other end thereof and an adjustable length suspension line therebetween, the suspension line being formed into at least two loops, engaged the said anchoring means, wherein the engagement portion or the anchoring means comprises a sleeve portion through which the ends of at least a first of the said at least two loops are threaded in opposite directions to cross over in the sleeve portion and emerge at opposite ends of the said sleeve portion.

The suspension line may incorporate any one or more of the features of the first aspect of the invention and may be produced in accordance with the method or any one or more of the preferred features of the method of the second aspect of the present invention. It will be appreciated that the sleeve portion may engage directly with the member to be tensioned or may form part of the anchor and, in either case, serve the purpose of allowing loop shortening and maintaining tension after shortening.

The adjustable loop may be adjusted in the same manner as that previously described with respect to the graft suspension device and is, also, preferably formed from a braided textile. Such a braided textile is preferably formed from two or more plaited threads so as to form a hollow tubular material which provides the necessary features for the cradle or sleeve portion of the tensioning device.

One possible application for the adjustable loop tensioning device is for tensioning of ligaments at the tibia bone hole during ACL fixation. Presently, sutures attached to the ends of the graft material protrude through the tibia bone hole and are tensioned prior to tying off or fixation. The adjustable loop of this aspect of the invention may be used to assist tensioning at the tibia bone hole. In such an application, it is possible that the anchoring means may be the foot of the patient so that it is envisaged that such an adjustable loop may be considerably longer than that used as a graft suspension device in the previous aspects of the invention.

Examples of grafts for use in the invention include ligament or tendon, in particular, reconstructed ligament or tendon.

The invention extends to a method of soft tissue—bone fixation utilising the graft suspension device. In particular, ligament or tendon fixation at a suitable joint such as the knee, elbow or shoulder. The invention is particularly advantageous in reconstruction of the anterior cruciate ligament (ACL) in the knee or the posterior cruciate ligament (PCL) in the knee. In particular, femoral fixation of the reconstructed ligament.

Preferably, the loose ends of the suspension device are sufficiently elongate, after passing through the cradle, to extend below the entrance to the bone tunnel to ease adjustment thereof by the surgeon. Preferably, the method includes locating at least two elongate grafts over the cradle and typically, loop adjustment pre-operatively and/or possibly, intra-operatively.

Preferably, the suture may be made from a suitable bio-compatible material. For instance, the material may be bio-absorbable material or a non-absorbable permanent material.

BRIEF DESCRIPTION OF THE DRAWINGS

An embodiment of the invention will now be described by way of example, with reference to the accompanying drawings in which.

DETAILED DESCRIPTION OF THE PREFERRED EMBODIMENT

Figure 1:
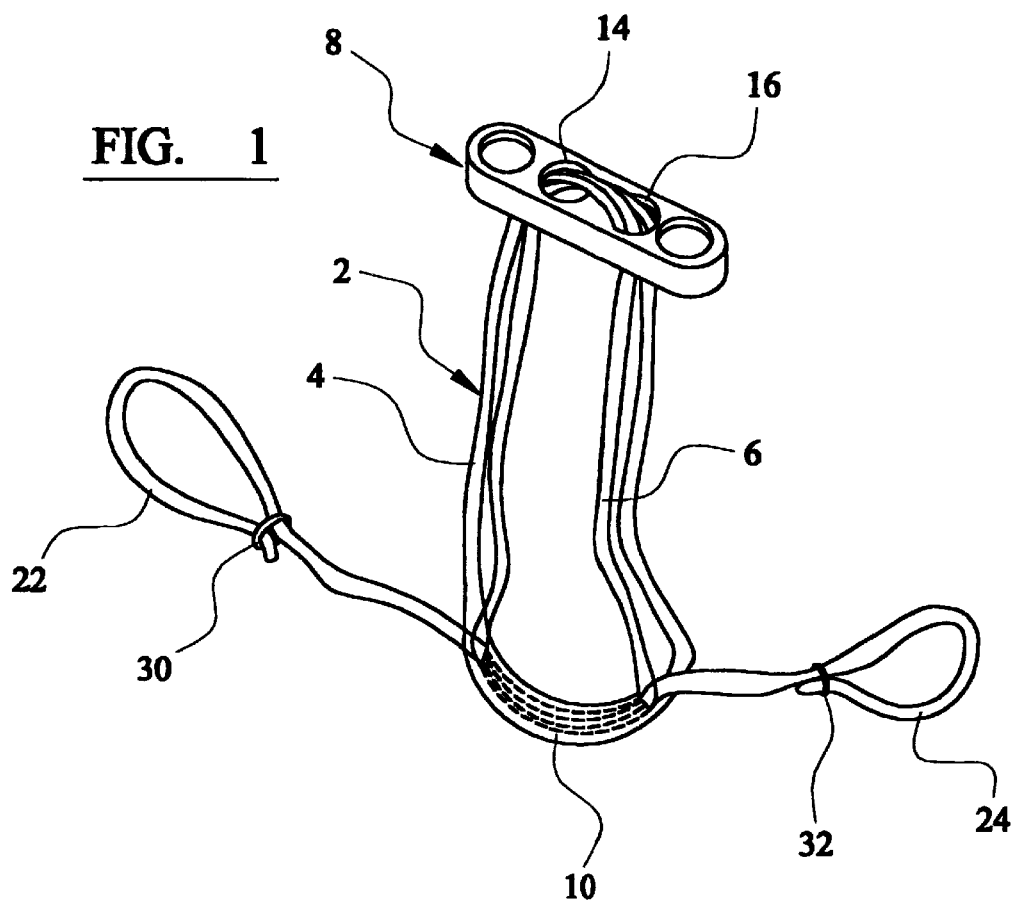
FIG. 1 shows a suture suspension loop attached to an anchor in accordance with the present invention.
Figure 2:
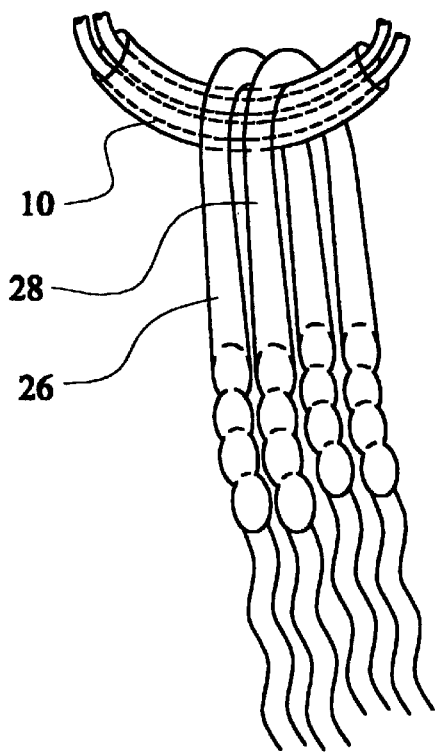
FIG. 2 shows a graft suspended over the cradle portion of a suspension loop in accordance with the present invention.
Figure 3:
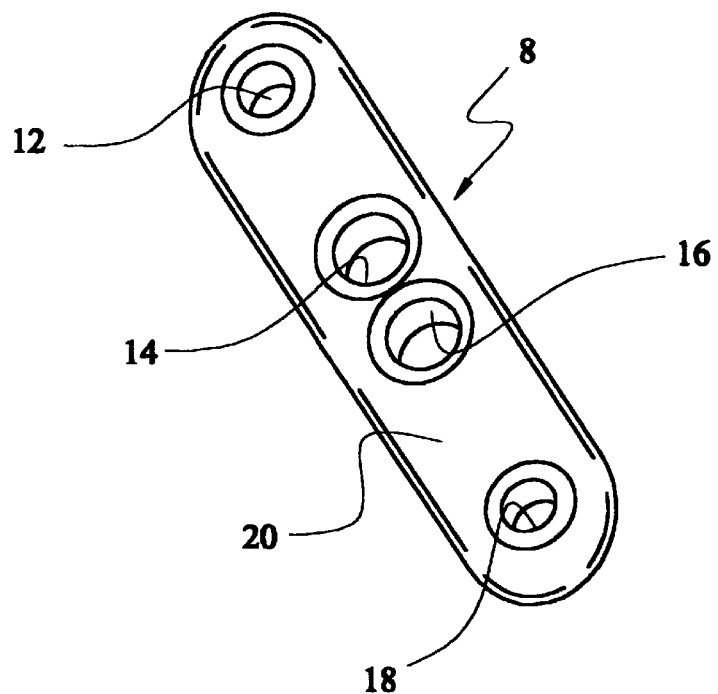
FIG. 3 shows an embodiment of an anchor for use with the present invention.

Referring to FIGS. 1, 2 and 3, a loop suspension device 2 comprises a first loop 4 and a second loop 6 suspended from an anchor 8 and having a cradle 10 at the opposite end of the loop to the anchor 8. The anchor 8 includes four circular apertures therethrough 12, 14, 16, 18. The body of the anchor 8 comprises a bar 20. The bar 20 has corners which have been chamfered at the corners in the longitudinal direction to give a smooth semi-circular face at either end thereof. The bar is straight and has four apertures aligned with each other along the longitudinal axis of the bar. The central pair of apertures 14, 16 are designed to accommodate the suture loops therethrough whereas the end apertures 12, 18 are designed for fixation of the anchor in position on the outside of a bone such as the femur. In FIG. 1, loops 4, 6 are shown threaded through the central pair of apertures 14, 16. The loose end finger loops 22, 24 are shown threaded through the hollow cradle 10 to complete the first loop 6. The threading of the loose ends in this manner has the effect of widening the cradle with respect to the remainder of the loop 4.

In FIG. 2, a pair of ligament grafts 26, 28 are shown looped over the cradle 10 midway along the length thereof. The wider cradle portion prevents the sutures cutting into the graft material during the grafting process.

With particular reference to FIG. 1, the method of providing the loop shown involves threading the loose ends 30, 32 through a respective aperture of the pair of central apertures 14, 16 of the anchor 8 from the underside to the top side thereof. More particularly, loose end 30 is threaded through aperture 14 and loose end 32 is threaded through aperture 16. Each loose end is then looped back through the other central aperture adjacent to the central aperture through which it has already been passed so that the loose end 32 passes through aperture 14 from the top side to the underside thereof and loose end 30 passes through aperture 16 from the top side to the underside thereof. Thereafter, loose end 30 is threaded through cradle portion 10 in the same direction as that from central aperture 16 to central aperture 14 and loose end 32 is also threaded through cradle 10 in the opposite direction equivalent to the direction from central aperture 14 to central aperture 16. At this stage, the threading process is complete and each loose end is itself tied into a finger loop 22, 24 to provide a means whereby the surgeon can adjust the distance of the cradle 10 from the anchor 8 thereby tensioning the grafts 26, 28 and/or shortening the loop length either before or during the surgical operation. The suture 2 is formed from a braided material having six plaited threads which together form a hollow tubular material. The cradle portion 10 may be threaded from either end thereof so that the loose ends 30, 32 may be passed through the central hollow portion of the suture to provide the thicker cradle portion 10. In use, by moving each finger loop 22, 24 away from the cradle portion 10, the length of the loops 4, 6 is shortened and, in this manner, the tensioning of the grafts 26, 28 may take place. Uniquely, although the length of the loops 4, 6 may be shortened in this manner release of the finger loops, 22, 24 after shortening, does not cause the loops to re-lengthen. In this manner, the surgeon can adjust the grafts to the required tension and then, tie-off subsequently, without the tension of the grafts being lost in the intervening period.

One method of attaching a graft is that used in reconstructing the Anterior Cruciate Ligament (ACL) or the Posterior Cruciate Ligament (PCL). Initially, notchplasty is carried out at the intercondylar notch. This technique is described in U.S. Pat. No. 5,139,520 (Rosenberg), which is incorporated herein by reference, and is known to those skilled in the art. Typically, with reference to FIG. 3, a drill guide is used to form a tibial channel 68. The isometric position required at the femoral surface is located using conventional surgical techniques and a closed end socket 70 is formed in the femur extending from the intercondylar notch at the angle required for ACL fixation. The length of the socket is relatively short and of the order of 2–3 cm. A pair of reconstructed ligaments have been located over the suture loop cradle 10 as previously described and the loop adjusted before being threaded, anchor first, up through the bone hole so that the ligaments are suspended therein with the anchor being passed through the suture passing channel and fixed at the opposite side of the bone.

Figure 4:
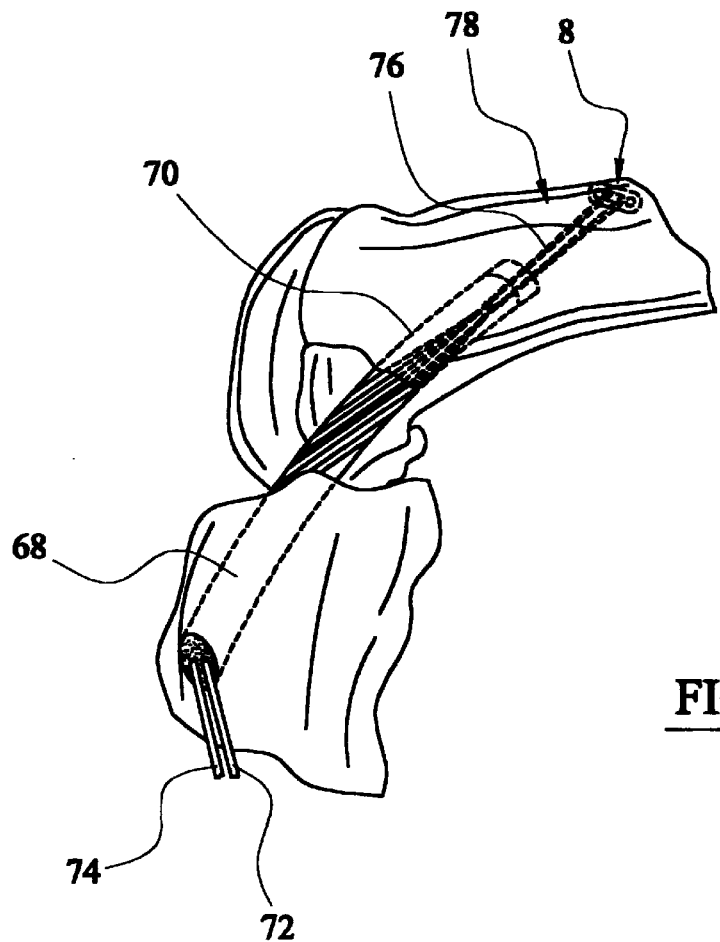
FIG. 4 shows a side view of the femur and tibia during graft location.

A method of carrying out use of the invention using conventional techniques is now described with reference to FIG. 4. Such conventional techniques have been described in European patent no. 0440991 (Rosenberg), the contents of which, insofar as they relate to the fixation of grafts using suture loops are incorporated herein by reference.

In one example of ACL fixation, an optimal site for drilling the femoral tunnel is determined through use of a suture anchor 8 and isometer (not shown). A pilot hole 76 is formed preferably with a wire device having means for limiting the depth of the hole. If required, the isometric point may be determined, the closed-end tunnel 70 may be drilled into the femur 78 at that point, using a new drill bit (not shown) having a small shank, an abbreviated drilling head, and a smooth transition portion between the shank and head. The graft is secured in the closed-end femoral tunnel 70 by means of a suture passing channel and a button and to the front of the tibia by a suitable conventional technique.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extend to any novel one, or any novel combination, of the features disclosed is in this specification (including any accompanying claims, abstract and drawings), or to any novel one, or any novel combination, of the steps of any method or process so disclosed.

What is claimed is:

1. A graft suspension device for a ligament fixation graft comprising suspension means for suspending a ligament in a bone hole, the suspension means having anchoring means at one end thereof, ligament cradling means at the other end thereof and an adjustable length suspension line therebetween, the suspension line being formed into at least two loops engaging the said anchoring means, wherein the cradling means comprises a sleeve portion through which the ends of at least a first of the said at least two loops are threaded in opposite directions to cross-over in the sleeve portion and emerge at opposite ends of the said sleeve portion.

2. A graft suspension device according to claim 1, wherein the sleeve portion forms part of a second of the said at least two loops.

3. A graft suspension device according to claim 1, wherein the sleeve portion forms an integral part of the said second loop.

4. A graft suspension device according to claim 1, wherein the sleeve portion is part of a second hollow loop whereby inlet and outlet eyes are formed in the hollow loop at spaced intervals to thereby form a sleeve portion through which the ends of the said first loop are threaded.

5. A graft suspension device according to claim 1, wherein the ends of the suspension line remain separate from each other.

6. A graft suspension device according to claim 1, wherein the ends of the line are adapted to include gripping elements to allow each end to be held and adjusted with respect to the sleeve portion to thereby effect shortening of the overall loop length and tensioning of the ligament.

7. A graft suspension device according to claim 1, wherein the loops of the suspension line are formed from a single line so that a loop is formed and then threaded back through the anchor to form a further loop which is completed by threading through the sleeve so that the ends of the further loop cross over therein.

8. A graft suspension device according to claim 1, wherein the suspension line is a suture.

9. A graft suspension device according to claim 8, wherein the suspension line is a hollow suture comprising a plurality of threads, the threads being plaited together to form a hollow tubular suture such as a braided suture.

10. A graft suspension device according to claim 1, wherein the sleeve portion is sufficiently long to suspendingly accommodate a ligament fixation graft thereover but sufficiently short to facilitate efficient adjustment of the suspension line length by urging the ends of the said first loop away from the said sleeve portion.

11. A graft suspension device according to claim 1, wherein the anchoring means is adapted to be secured to the outside of the opposite side of the bone to the opening to the bone tunnel.

12. A graft suspension device according to claim 1, wherein the anchoring means is adapted for securement to the outside of a bone.

13. A graft suspension device according to claim 1, wherein the anchoring means includes a pair of apertures through which the ends of the suspension line may be threaded during loop formation.

14. A graft suspension device according to claim 1, wherein the cradle is formed by the space between the pair of apertures in the hollow suture.

15. A graft suspension device for a ligament fixation graft comprising:

a suspension device for suspending a ligament in a bone hole, the suspension device having an anchor at one end thereof;

a ligament cradle at the other end of the suspension device;

an adjustable length suspension line extending between the anchor and the ligament cradle, the suspension line being formed into at least two loops engaging the anchor;

wherein the cradle comprises a sleeve portion through which the ends of at least a first of the at least two loops are threaded in opposite directions to cross-over in the sleeve portion and emerge at opposite ends of the sleeve portion the sleeve portion is structured so the first loop, while under tension, does not significantly re-extend after the first loop is adjustably shortened.

* * * * *